United States Patent [19]
Huo et al.

[11] Patent Number: 6,066,172
[45] Date of Patent: May 23, 2000

[54] INJECTABLE INTRAOCULAR LENS

[75] Inventors: Peter P. Huo; Stephen Q. Zhou; Christine J. Y. Liau, all of Irvine, Calif.; Sverker Norrby, Leel, Netherlands

[73] Assignee: Pharmacia & Upjohn AB, Stockholm, Sweden

[21] Appl. No.: 09/170,160

[22] Filed: Oct. 13, 1998

[51] Int. Cl.[7] .......................................................... A61F 2/16

[52] U.S. Cl. ........................ 623/6.56; 623/6.11; 623/6.13; 528/10; 264/1.1

[58] Field of Search ................................... 623/6.11, 6.13, 623/6.56; 525/474; 528/10; 523/107, 113; 264/1.1

[56] References Cited

U.S. PATENT DOCUMENTS

| | | |
|---|---|---|
| 5,278,258 | 1/1994 | Gerace et al. . |
| 5,316,704 | 5/1994 | Wang et al. . |
| 5,391,590 | 2/1995 | Gerace et al. . |
| 5,411,553 | 5/1995 | Gerace et al. . |
| 5,476,515 | 12/1995 | Kelman et al. . |
| 5,643,275 | 7/1997 | Blake . |
| 5,702,441 | 12/1997 | Zhou . |

*Primary Examiner*—Dinh X. Nguyen
*Attorney, Agent, or Firm*—Oppenheimer Wolff & Donnelly LLP

[57] ABSTRACT

An injectable intraocular lens composed of a silicone material is disclosed. The silicone lens material is polymerized from a plurality of siloxane monomers. The silicone lens material has a specific gravity great than 1.0 and a refractive index of a natural lens.

19 Claims, No Drawings

INJECTABLE INTRAOCULAR LENS

BACKGROUND OF THE INVENTION

The present invention relates an intraocular lens and to materials useful in making intraocular lenses (IOLs), specifically, injectable IOLs, and methods for their preparation. More particularly, this invention relates to high specific gravity silicone materials suitable for making accommodative IOLs which can be injected with greater convenience than current materials.

The human eye is a highly evolved and complex sensory organ. It is composed of a cornea, or clear outer tissue which refracts light rays enroute to the pupil, an iris which controls the size of the pupil thus regulating the amount of light entering the eye, and a lens which focuses the incoming light through the vitreous fluid to the retina. The retina converts the incoming light into electrical energy that is transmitted through the brain stem to the occipital cortex resulting in a visual image. In the perfect eye the light path from the cornea, through the lens and vitreous fluid to the retina is unobstructed. Any obstruction or loss in clarity within these structures causes scattering or absorption of light rays resulting in diminished visual acuity. For example, the cornea can become damaged resulting in edema, scarring or abrasions, the lens is susceptible to oxidative damage, trauma and infection, and the vitreous can become cloudy due to hemorrhage or inflammation.

As the body ages, the effects of oxidative damage caused by environmental exposure and endogenous free radical production accumulate resulting in a loss of lens flexibility and denatured proteins that slowly coagulate reducing lens transparency. The natural flexibility of the lens is essential for focusing light onto the retina by a process referred to as accommodation. Accommodation allows the eye to automatically adjust the field of vision for objects at different distances. A common condition known as presbyopia results when the cumulative effects of oxidative damage diminish this flexibility reducing near vision acuity. Presbyopia usually begins to occur in adults during their mid-forties; mild forms are treated with glasses or contact lenses.

Lenticular cataracts is a lens disorder resulting from protein coagulation and calcification. There are four common types of cataracts: senile cataracts associated with aging and oxidative stress, traumatic cataracts which develop after a foreign body enters the lens capsule or following intense exposure to ionizing radiation or infrared rays, complicated cataracts which are secondary to diseases such as diabetes mellitus or eye disorders such as detached retinas, glaucoma and retinitis pigmentosa, and toxic cataracts resulting from medicinal or chemical toxicity. Regardless of the cause, the disease results in impaired vision and may lead to blindness.

Treatment of severe lens disease requires the lens' surgical removal or pharmacoemultion followed by irrigation and aspiration. However, without a lens the eye is unable to focus the incoming light on the retina. Consequently, artificial lenses must be used to restore vision. Three types of prosthetic lenses are available: cataract glasses, external contact lenses and IOLs. Cataract glasses have thick lenses, are uncomfortably heavy and cause vision artifacts such as central image magnification and side vision distortion. Contact lenses resolve many of the problems associated with glasses, but require frequent cleaning, are difficult to handle (especially for elderly patients with symptoms of arthritis), and are not suited for persons who have restricted tear production. Intraocular lenses are used in the majority of cases to overcome the aforementioned difficulties associated with cataract glasses and contact lenses.

There are four primary IOL categories: non-deformable, foldable, expansible hydrogels and injectable. Early non-deformable IOL implants were ridged structures composed of acrylates and methacrylates requiring a large incision in the capsular sac and were not accommodative. This large incision resulted in protracted recovery times and considerable discomfort for the patient. In an effort to reduce recovery time and patient discomfort numerous small incision technique and lenses have been developed.

Early lenses designed for small incision implantation were elastomeric compositions that could be rolled or folded, inserted into the capsular sac then unfolded once inside. Occasionally, the fold of the lens before insertion resulted in permanent deformation adversely effecting the implant's optical qualities. Foldable lenses overcame the need for the large incision non-deformal deformable lenses required, but were not accommodative. Moreover, both non-deformable and foldable IOLs are susceptible to mechanical dislocation resulting in damage to the corneal endothelium.

Another approach to small incision IOL implantation uses an elastomeric polymer that becomes pliable when heated to body temperature or slightly above. Once pliable, the lens is deformed along a least one axis reducing its size sufficient for easy insertion through a small incision. The lens is then cooled to retain the modified shape until re-heated. The cooled lens is inserted into the capsular sac and the natural body temperature warms the lens and it returns to its original shape. The primary drawback to the thermoplastic lens is the limited number of polymers that meet the exacting needs of this approach. Most polymers are composed of polymethylacyrlate which have solid-liquid transition temperatures above 100° C. Modifications of the polymer substrate requires the use of plastisizers that may eventually leach into the eye.

Dehydrated hydrogels have also been used with small incisions techniques. Hydrogel lenses are dehydrated before insertion and naturally rehydrated once inside the capsular sac. However, once fully rehydrated the polymer structure is notoriously weak due to the large amount of water absorbed. The typical dehydrated hydrogel's diameter will expand from 3 mm to 6 mm resulting in a lens that is 85% water. At this water concentration the refractive index drops to approximately 1.36 which is unacceptable for an IOL. To achieve a refractive index between 1.405 to 1.410 a significantly thicker lens is required; this is even further exacerbated when lees diameters exceed 6 mm.

Recent technological advances have led to the development of injectable IOLs. This lens category is injected directly into the empty capsular sac and cured in situ. Unlike conventional IOLs that are fabricated and shaped before implantation, injectable IOLs are formed inside the eye itself. Once cured, the IOL assumes the shape and exact dimensions of the natural lens. A further advantage to injectable IOLs is that an incision as small as 1.5 mm can be used to remove the natural lens and inject the IOL.

The only silicone material currently used for injectable IOLs is polydimethylsiloxane (PDMS). This silicon material has a refractive index similar to the natural lens and has been used successfully with foldable silicone implants. However, it has been reported that injectable lenses fabricated from PDMS exhibit undesirable qualities associated with its specific gravity. Current PDMS compounds have a specific gravity less than 1.0 and float on the aqueous layer when injected into the capsular sac. This physical property makes it tremendously difficult to fill the capsular sac completely and requires the surgeon to manually express water in order to maintain the correct lens shape during the curing process. Therefore, it is desirable to formulate an injectable lens made from a compound with a specific gravity greater that 1.0, while maintaining the refractive indices of natural lenses.

There have been numerous attempts to develop materials suitable for use as injectable IOLs. For example, Gerace et al. describe a fast curing mixture of vinyl-containing polyorganosiloxane, organosilicone and a platinum group metal catalyst used to form an IOL in their U.S. Pat. Nos. 5,278,258, 5,391,590 ('590) and 5,411,553 patents. The resulting polymers demonstrate a reduced tendency to discolor characteristic of other platinum catalyzed silicon polymers. The '590 patent so discloses a substantially non-functional polymer component of the mixture that has a viscosity at least 50 times greater than the functional polymers. The non-functional component is mixed with the functional components to adjust viscosity to a pre-determined specification.

Kelman discloses an injectable collagen IOL in U.S. Pat. No. 5,476,515. This lens is clear, resist to epithelialation and is capable of accommodation. It is made from a transparent collagen compound that has a refractive index range from 1.2 to 1.6 that can be used in either its original viscous state, or polymerized into a soft gel. The collagen compound is injected directly into the capsular sac following natural lens removal.

Efforts to develop suitable injectable IOLs disclosed in the references cited above were directed at resolving deficiencies in existing silicon material chemistry and the development of new non-silicon based materials. However, to the best of our knowledge, no silicon material suitable for use as an injectable IOL has been described that possesses the combined properties of a specific gravity greater than 1.0, an optically smooth surface and a refractive index of a natural lens.

OBJECTS AND SUMMARY OF THE INVENTION

The objects of the present invention are to provide materials useful in making IOLs, specifically, injectable IOLs, and methods for their preparation and use. In particular it is an object of the present invention to provide an intraocular lenses having the advantage of a specific gravity greater than 1.0 that greatly simplifies implantation and helps to assure proper positioning and conformation once cured in situ. Another objective of this invention is to provide a silicone polymer IOL that has a refractive index within the physiological range the recipient requires for proper vision and a specific gravity greater than 1.0. A further object is to provide materials and methods that lead to a fully cured injectable IOL with an optically smooth surface.

These and other objects not specifically enumerated are addressed by identifying high specific gravity silicone materials suitable for making accommodative IOLs that can be injected with greater convenience than current materials. These high specific gravity silicone materials are prepared from a mixture of siloxane compounds including either trimers, tetramers or higher order cyclic siloxanes. The monomeres used in the preferred embodiments of the present invention include, but are not limited to, methyl and substituted methyl siloxanes, phenyl siloxane and trifluoropropyl methylsiloxanes having individual specific gravities ranging between 0.97 and 1.24.

A terpolymeric IOL with a precise refractive index and specific gravity can be prepared by mixing three siloxane monomers in a predetermined ratio. Once formed the polymer has a specific cavity greater than 1.0 and can be injected into the patient's previously prepared capsular sac and cured in situ. During the curing process intraocular pressure is maintained at approximately 10 mm of mercury to assure proper lens positioning and conformation within the capsular sac. The resulting IOL will have a refractive index within the physiologic range previously determined optimum for the given application and an optically smooth surface.

DETAILED DESCRIPTION OF EXEMPLARY EMBODIMENTS

This invention relates to methods and materials for co-polymerized siloxane monomers such that the resulting silicone material has a specific gravity greater than 1.0 and a refractive index ranging from 1.385 to 1.685. The present invention also provides methods and materials that can be used to either replace a damaged or diseased ocular lens, or correct impaired vision. More specifically, the materials and methods described form high specific gravity silicone polymers suitable for forming IOLs cured in situ that are transparent and have refractive indices capable of restoring the recipient's normal vision. The silicone co-polymers formed by the methods of the present invention are particularly well suited for use as injectable IOLs.

The present invention is based on the discovery that materials currently used for injectable IOLs have a specific gravities below 1.0 and float when injected into the capsular sac's aqueous environment. Buoyant prosthetic lens materials injected into the patients capsular sac require residual water to be mechanically displaced to assure the IOL's proper positioning and conformation. The high specific gravity materials described in the present invention displace water when injected into the capsular sac reducing post injection manipulation and assure that the lens will assume a natural position and configuration.

In accordance with the methods of the present invention an injectable IOL material is formed that greatly simplifies the injection, positioning and curing process. Consequently, an incision size considerably less than traditionally required is employed. Prior art foldable IOLs required 3 to 4 mm surgical incision. While this is substantially less than the incision associated older style non-foldable lenses, it is twice the size required by the present invention. Thus, the methods described herein significantly reduce the patient's surgical discomfort and post surgical recovery time.

Another advantage of this invention is the extremely compliant nature of the fully cured lens. If a conventional foldable silicone lens is considered to have a stiffness of 100, a cured injectable lens made from the material of the present invention would have a stiffness ranging from zero five. Therefore, lenses made from the material described herein are accommodative and respond naturally to the changes in the eyes' shape as focal length is adjusted. The accommodative nature of lenses fabricated from materials of the present invention makes them particularly suitable for corrective purposes besides replacements for diseased natural lenses and is considered within the scope of this invention. An unexpected, and beneficial, advantage of the present invention is the optically smooth surface formed after the lens has cured in situ.

The types of siloxane monomers useful in preparing the IOLs of this preferred embodiment include, but are not limited to, methyl and substituted methyl siloxanes, phenyl siloxanes and trifluoropropyl methyl siloxanes with individual specific gravities ranging between 0.97 and 1.24. The high specific gravity silicone co-polymers of the present invention are prepared by mixing a plurality of these compounds in a predetermined ratio to achieve a desired specific cavity and refractive index. More specifically, three siloxane monomers are mixed together with a suitable end blocker and dried in a reduced atmosphere under controlled thermal conditions. The reaction mixture is then catalyzed to induce co-polymerization in an inert atmosphere. The reaction is allowed to continue for a predetermined time in a precise thermal environment then terminated. Next, the reaction product is washed, precipitated and dried. The specific gravity, refractive index and mean molecular weight are determined.

In another embodiment of the present invention three siloxane monomers are mixed together with a suitable end blocker and dried in a reduced atmosphere under controlled thermal conditions as before. The reaction mixture is then catalyzed to induce co-polymerization in an inert atmosphere. The reaction is allowed to continue for a predetermined time in a precise thermal environment then terminated. Next, the reaction product is washed, precipitated and dried. The resulting precipitate is then re-dissolved in a suitable solvent and filtered to enhance clarity. The specific gravity, refractive index and mean molecular weight are determined. Change in the reactants, their relative concentrations and reaction conditions will result in a variety of end products with different specific gravities and refractive indices. The benefits of these differences will become apparent to one skilled in the art from the specific examples below.

According to the methods of the present invention, the ratio of siloxane monomer reactants necessary to achieve a desired refractive index and specific gravity can be approximated mathematically. If N is the desired IOL's refractive index and P is the specific gravity of the lens' copolymer and where $n_{1-3}$ are the refractive indices and $p_{1-3}$ are the specific gravities of the monomer reactants then the following mathematical relationship has been determined to exist:

$$N = x_1 n_1 + x_2 n_2 + x_3 n_3$$

$$P = x_1 p_1 + x_2 p_2 + x_3 p_3$$

Where $x_{1-3}$ present the ratio of the individual siloxane monomer reactants required to achieve an IOL with the desired optical and physical properties and $x_1 + x_2 + x_3 = 1$.

Having an injectable silicone lens with a specific gravity greater than 1.0 would greatly simplify the injection process and represents a significant improvement over current injectable PDMS lenses. Prosthetic lenses made by the process described herein are compliant and retain the refractive index of the natural lens making them ideal as corrective lenses as well as replacements for damaged and cataractous lenses.

The following examples are offered as being illustrative of the principles of the present invention and not by way of limitation.

EXAMPLE 1

A mixture containing 6 grams of hexylmethyl cyclotrisiloxane, 7.3 grams of 3,3,3-trifluoropropylmethyl cyclotrisiloxane, 1.7 grams (1.55 ml) of 1,3,5-trimethyl-1,3,5-tri phenyl cyclotrisiloxane and 0.14 grams (0.17 ml) of an end blocker such as 1,3-divinyltetramethyldisiloxane was added to a 50 mL flask. The mixture was dried at 80° C. under a vacuum for 30 minutes and then purged with argon gas. The temperature of the dried mixture was raise to 140° C. and about 7 mg of potassium silanoate was added to the mixture to initiate a polymerization reaction. The reaction proceeded quickly producing a high molecular weight polymer with an elevated viscosity. About 30 minutes later this high molecular weight polymer became a glass clear cyclic polymer and viscosity decreased.

Two hours later the viscosity of the reaction mixture had increased again. The temperature was then elevated to 160° C. for about three hours and terminated by decreasing the reaction temperature to room temperature. The polymer product was washed with tetrahydrofuran (THF), precipitated with methanol and dried. After drying the silicone polymer product was glass clear, the refractive index was 1.4070, the specific gravity was 1.116 and the average molecular weight (MW) was 25,000. Cross-linking the polymer product produced a clear silicon gel.

EXAMPLE 2

A polymer product was prepared according to Example 1 except that twice the amount of end blocker was used. The silicone reaction product was glass clear. The refractive index was 1.4074, the specific gravity was 1.116 and the MW was 15,000 which was consistent with the amount of end blocker used.

EXAMPLE 3

A reaction mixture was prepared according to Example 1 except that the siloxane monomers were substituted with 9 grams of hexylmethyl cyclotrisiloxane, 4.65 grams of 3,3,3-trifluoroproylmethyl cyclotrisiloxane and 1.35 grams (1.23 ml) of 1,3,5-trimethyl-1,3,5-triphenyl cyclotrisiloxane. The resulting silicone polymer product was glass clear, the refractive index was 1.4082, the specific gravity was 1.066 and the MW was 26,000.

EXAMPLE 4

A fixture containing 7.5 grams of hexylmethyl cyclotrisiloxane, 6.66 grams of 3,3,3-trifluoroproylmethyl cyclotrisiloxane, 1.68 grams of hexylphenyl cyclotrisiloxane, and 0.28 grams (0.34 ml) of an end blocker such as 1,3 divinyltetramethyldisiloxane was added to a 50 mL reaction flask. The mixture was dried at 80° C. under vacuum for thirty minutes and then purged with argon gas. The temperature was then raised to 160° C. and about 7 mg of potassium silanoate was added. The catalyst addition accelerated the polymerization rate forming a high molecular weight polymer with increased viscosity. About thirty minutes later, the high molecular weight polymer started to become cyclic. The solution was almost clear with some residue at the bottom of the reaction vessel. The viscosity of the reaction mixture was decreasing.

After about two hours the polymer's viscosity had increased and the temperature was raised to 160° C. Approximately three hours later the reaction was terminated by decreasing the temperature to room temperature. The polymer was washed with THF and precipitated with methanol. After being dried, the silicone material was slightly hazy. The material was then redissolved with THF and filtered through a 0.45 micrometer filter. Drying the filtered solution yielded a glass clear silicone material. The refractive index was 1.4095, the specific gravity was 1.10 and the MW was 18,000. Cross-linking this material yielded a clear silicone gel.

EXAMPLE 5

A mixture containing 7.5 grams of octamethyl cyclotetrasiloxane and higher order cyclics (dimethylsiloxane cyclics), 6.66 grams of 3,3,3-trifluoropropylmethyl cyclotrisiloxane, 1.68 grams of octaphenyl cyclotetrasiloxane, and 0.28 grams (0.34 ml) of an end blocker such as 1,3 divinyltetramethyldisiloxane was added to a 50 mL reaction flask. The resulting reaction mixture was dried at 80° C. under vacuum for thirty minutes and then purged with argon gas. The temperature was raised to 160° C. and about 7 mg of potassium silanoate was added. The catalyst addition accelerated the polymerization rate forming a high molecular weight polymer with increased viscosity. About thirty minutes later this high molecular weight polymer started to become cyclic and its viscosity was decreasing. It was glass clear with no residue at the bottom of the reaction vessel. After approximately two hours the viscosity had increased and the temperature was raised to 160° C.. About three hours later the reaction was terminated by decreasing the temperature to room temperature. The polymer was washed with THF and then precipitated with methanol. After drying, the silicone material was glass clear. The refractive index was 1.4103, the specific gravity was 1.10 and the MW was 15,000. Cross-linking this material yielded a clear silicone gel.

Having thus described exemplary embodiments of the present invention, it should be noted by those skilled in the art that the disclosures herein are exemplary only and that alternatives, adaptations and modifications may be made within the scope of the present invention.

What is claimed is:

1. An injectable silicone lens material, comprising:
   a silicone material having a specific gravity that is greater than 1.0 and a refractive index of a natural lens that is polymerized from a plurality of siloxane monomers.
2. The injectable silicone lens material of claim 1 wherein the refractive index ranges between 1.383 and 1.695.
3. The injectable silicone lens material of claim 1 wherein at least one siloxane monomer has a specific gravity greater than 1.0.
4. The injectable silicone lens material of claim 1 wherein the silicone is a terpolymer having a specific gravity of about 1.1 and a refractive index of about 1.41.
5. The injectable silicone lens material of claim 1 wherein the silicone is a copolymer having a specific gravity of about 1.1 and a refractive index of about 1.41.
6. A reaction mixture for making a lens material, comprising:
   a plurality of siloxane monomers having a specific gravity ranging from 0.97 to 1.24 wherein the siloxane monomers comprise one or more trimer or tetramer or higher order cyclic siloxane monomers forming a silicone lens material with a specific gravity greater than 1.0.
7. The reaction mixture of claim 6 wherein the plurality of siloxane monomers is copolymerized to make a terpolymer with a refractive index of about 1.41 and a specific gravity of about 1.1.
8. The reaction mixture of claim 6 wherein at least one of the monomers has a specific gravity that is greater than 1.0.
9. The reaction mixture of claim 6 wherein the plurality of siloxane monomers are selected from a group consisting of methyl and substituted methyl siloxanes, phenyl siloxanes and trifluoropropyl methyl siloxane.
10. The reaction mixture of claim 6 wherein the plurality of siloxane monomers consists essentially of hexylmethy cyclotrislioxane, 3,3,3-trifluoropropylmethyl cyclotrisiloxane and 1,3,5-trimethyl-1,3,5-triphenyl cyclotrisiloxane.
11. The reaction mixture of claim 6 wherein the plurality of siloxane monomers consists essentially of hexylmethy cyclotrislioxane, 3,3,3-trifluoropropylmethyl cyclotrisiloxane and hexylphenyl cyclotrisiloxane.
12. The reaction mixture of claim 6 wherein the plurality of siloxane monomers consists essentially of octamethyl cyclotetrasiloxane and higher order cyclics (dimethylsiloxane cyclics), 3,3,3-trifluoropropylmethyl cyclotrisiloxane and octaphenyl cyclotetrasiloxane.
13. A method of making an injectable silicone lens, comprising:
   providing a plurality of siloxane monomers each having a specific gravity within a range of 0.97 to 1.24;
   polymerizing the siloxane monomers to form a polymer having a specific gravity greater than 1.0; and
   curing by transferring the polymerized siloxane monomers to a capsular sac to make an intraocular implant.
14. The method of claim 13 wherein the polymerized siloxane monomers have a refractive index within a range of 1.383 to 1.695.
15. The method of claim 13 wherein the siloxane monomers are selected from a group consisting of trimers, terameres and higher cyclic siloxanes.
16. The method of making an injectable silicone lens of claim 13 wherein the plurality of siloxane monomers consists essentially of hexylmethy cyclotrislioxane, 3,3,3-trifluoropropylmethyl cyclotrisiloxane and 1,3,5-trimethyl-1,3,5-triphenyl cyclotrisiloxane.
17. The method of making an injectable silicone lens of claim 13 wherein the plurality of siloxane monomers consists essentially of hexylmethy cyclotrislioxane, 3,3,3-trifluoropropylmethyl cyclotrisiloxane and hexylphenyl cyclotrisiloxane.
18. The method of making an injectable silicone lens of claim 13 wherein the plurality of siloxane monomers consists essentially of octamethyl cyclotetrasiloxane and higher order cyclics (dimethylsiloxane cyclics), 3,3,3-trifluoropropylmethyl cyclotrisiloxane and octaphenyl cyclotetrasiloxane.
19. An injectable intraocular lens comprising: a silicone terpolymer having a specific gravity greater than 1.0, said lens being cured in situ and having an optically smooth surface and refractive index ranging between 1.383 and 1.695.

* * * * *